(12) United States Patent
Ishikake

(10) Patent No.: US 11,900,615 B2
(45) Date of Patent: Feb. 13, 2024

(54) TRACKING DEVICE, ENDOSCOPE SYSTEM, AND TRACKING METHOD

(71) Applicant: OLYMPUS CORPORATION, Hachioji (JP)

(72) Inventor: Makoto Ishikake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 486 days.

(21) Appl. No.: 17/179,903

(22) Filed: Feb. 19, 2021

(65) Prior Publication Data
US 2021/0183076 A1 Jun. 17, 2021

Related U.S. Application Data

(63) Continuation of application No. PCT/JP2019/013606, filed on Mar. 28, 2019.

(51) Int. Cl.
*G06T 7/246* (2017.01)
*G06T 7/73* (2017.01)
(Continued)

(52) U.S. Cl.
CPC ............ *G06T 7/246* (2017.01); *A61B 1/0002* (2013.01); *A61B 5/7267* (2013.01); *G06T 7/73* (2017.01);
(Continued)

(58) Field of Classification Search
CPC .......... G06T 7/246; G06T 2207/10016; G06T 2207/20081; G06T 7/12; G06T 9/20;
(Continued)

(56) References Cited

U.S. PATENT DOCUMENTS 5,764,283 A * 6/1998 Pingali .................... G01S 11/12
348/169
5,999,651 A * 12/1999 Chang .................... G06T 7/246
382/199
(Continued)

FOREIGN PATENT DOCUMENTS

CN 101477690 A * 7/2009
CN 105761277 A * 7/2016
(Continued)

OTHER PUBLICATIONS

International Search Report (ISR1) dated Jun. 18, 2019, issued in counterpart International Application No. PCT/JP2019/013606, with English Translation. (4 pages).
(Continued)

*Primary Examiner* — Ian L Lemieux
*Assistant Examiner* — Woo C Rhim
(74) *Attorney, Agent, or Firm* — WHDA, LLP

(57) ABSTRACT

A tracking device includes a processor including hardware, and the processor sets a start frame, extracts multiple representative points of a contour of a tracking target, tracks the extracted multiple representative points, performs outlier determination based on an interrelationship of the tracked multiple representative points, performs a process of removing an outlier representative point determined to be an outlier, and extracts new representative points based on multiple representative points after the process of removing the outlier representative point when a given condition is met.

10 Claims, 17 Drawing Sheets

(51) Int. Cl.
*A61B 1/00* (2006.01)
*A61B 5/00* (2006.01)

(52) U.S. Cl.
CPC ... *A61B 1/000094* (2022.02); *A61B 1/000096* (2022.02); *G06T 2207/10016* (2013.01); *G06T 2207/10068* (2013.01); *G06T 2207/20081* (2013.01); *G06T 2207/30004* (2013.01)

(58) Field of Classification Search
CPC ............. G06T 2207/10068; G06T 7/73; G06T 2207/20084; G06T 2207/30004; A61B 1/0002; A61B 5/7267; A61B 1/000094; A61B 1/000096; A61B 5/004
See application file for complete search history.

(56) References Cited

U.S. PATENT DOCUMENTS

| | | | |
|---|---|---|---|
| 6,259,802 B1* | 7/2001 | Jolly | G06T 7/246 382/199 |
| 6,546,117 B1* | 4/2003 | Sun | G06V 10/755 375/E7.081 |
| 6,678,416 B1* | 1/2004 | Sun | G06T 7/251 382/235 |
| 6,912,310 B1* | 6/2005 | Park | G06V 10/24 382/199 |
| 6,937,760 B2* | 8/2005 | Schoepflin | G06T 7/155 382/199 |
| 9,478,033 B1* | 10/2016 | Safreed | G06T 7/251 |
| 2003/0171668 A1 | 9/2003 | Tsujino et al. | |
| 2004/0208341 A1 | 10/2004 | Zhou et al. | |
| 2006/0008138 A1* | 1/2006 | Zhou | G06V 10/7553 382/154 |
| 2006/0262960 A1* | 11/2006 | Le Clerc | G06V 10/24 348/E9.037 |
| 2008/0100709 A1* | 5/2008 | Furukawa | G01S 3/7865 348/169 |
| 2011/0052071 A1* | 3/2011 | Iwamoto | G06T 7/12 382/190 |
| 2011/0158474 A1* | 6/2011 | Srikrishnan | G06T 7/246 382/199 |
| 2012/0114173 A1* | 5/2012 | Ikenoue | G06T 7/246 382/199 |
| 2014/0010409 A1* | 1/2014 | Yamashita | G06V 10/752 382/103 |
| 2016/0055648 A1* | 2/2016 | Liu | H04N 23/80 382/103 |
| 2017/0111585 A1* | 4/2017 | Schlattmann | G06T 7/33 |
| 2017/0251998 A1 | 9/2017 | Maed et al. | |
| 2018/0165808 A1* | 6/2018 | Bagci | G06V 10/82 |
| 2018/0259608 A1 | 9/2018 | Golden et al. | |
| 2019/0197703 A1* | 6/2019 | Wang | G06V 20/41 |
| 2020/0074673 A1* | 3/2020 | Gupta | G06F 18/214 |
| 2020/0160540 A1* | 5/2020 | Rastgar | G06T 7/251 |
| 2020/0226781 A1* | 7/2020 | Ma | G06T 7/33 |
| 2020/0279373 A1* | 9/2020 | Hussain | A61B 1/000096 |
| 2021/0196101 A1 | 7/2021 | Usuda | |

FOREIGN PATENT DOCUMENTS

| | | | | |
|---|---|---|---|---|
| JP | 2002230548 A | * | 8/2002 | |
| JP | 2003-250804 A | | 9/2003 | |
| JP | 2003250804 A | * | 9/2003 | ........... A61B 8/0883 |
| JP | 2005-160688 A | | 6/2005 | |
| JP | 2007-222533 A | | 9/2007 | |
| JP | 2009037518 A | * | 2/2009 | |
| JP | 2016-55040 A | | 4/2016 | |
| JP | 6055565 B1 | | 12/2016 | |
| JP | 6055565 B1 | * | 12/2016 | |
| WO | 2004/081875 A2 | | 9/2004 | |
| WO | WO-2004081875 A2 | * | 9/2004 | ........... G06K 9/3216 |
| WO | WO-2017011833 A1 | * | 1/2017 | ......... H04L 63/1433 |
| WO | 2017/091833 A1 | | 6/2017 | |
| WO | 2017/158897 A1 | | 9/2017 | |
| WO | WO-2019022663 A1 | * | 1/2019 | ........... A61B 3/0025 |

OTHER PUBLICATIONS

International Search Report (ISR2) dated Jun. 18, 2019, issued in counterpart International Application No. PCT/JP2019/013607, with English Translation. (4 pages).
Related Co-pending U.S. Appl. No. 17/179,919.
Non-Final Office Action dated Jan. 3, 2023, issued in related co-pending U.S. Appl. No. 17/179,919. (24 pages).

\* cited by examiner

FIG. 10
BEFORE ANNOTATION
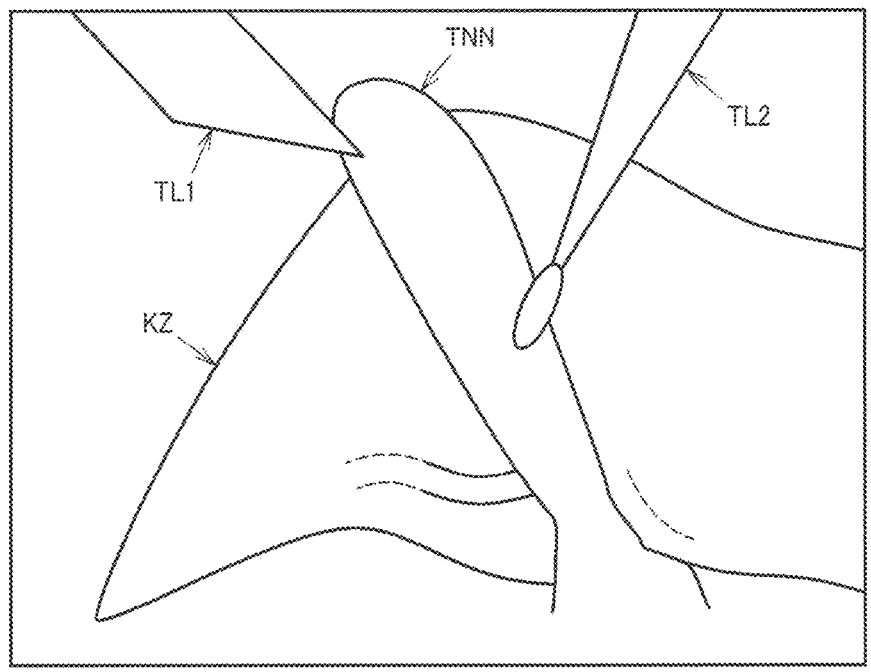
AFTER ANNOTATION
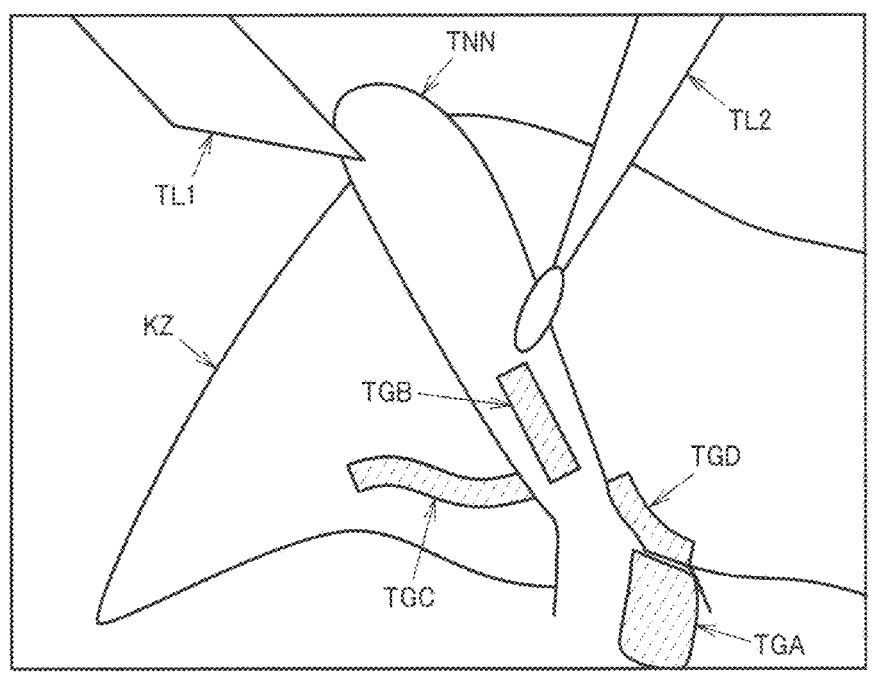

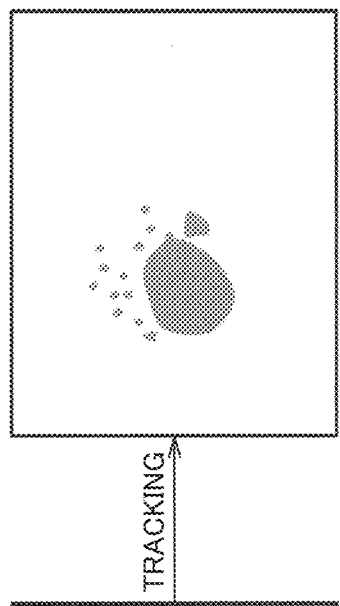
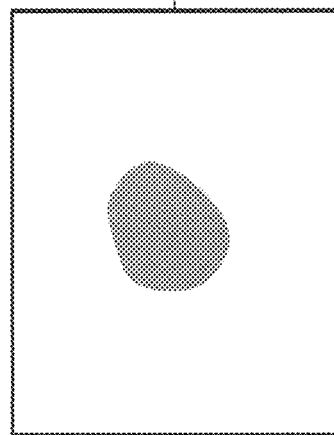

TRACKING DEVICE, ENDOSCOPE SYSTEM, AND TRACKING METHOD

CROSS REFERENCE TO RELATED APPLICATION

This application is a continuation of International Patent Application No. PCT/JP2019/013606, having an international filing date of Mar. 28, 2019, which designated the United States, the entirety of which is incorporated herein by reference.

BACKGROUND

There are conventional methods for estimating a location of a designated target in each frame image included in a video. Such methods are hereinafter referred to as tracking, and the designated target is hereinafter referred to as a tracking target. The tracking can be considered as a method for tracking how the tracking target has moved over multiple frame images.

For example, Japanese Unexamined Patent Application Publication No. 2007-222533 discloses a method for tracking an organ in a medical image by using contour points of the organ.

SUMMARY

In accordance with one of some aspect, a tracking device comprising a processor including hardware,
the processor being configured to:
set a start frame to start tracking of a tracking target in a video including multiple frames;
extract multiple representative points of a contour of the tracking target in the start frame;
track the extracted multiple representative points in frames subsequent to the start frame;
perform outlier determination on the tracked multiple representative points based on an interrelationship of the multiple representative points;
perform a process of removing an outlier representative point that is a representative point determined to be an outlier; and
update the representative points by extracting new representative points based on multiple representative points after the process of removing the outlier representative point, in a case where any frame subsequent to the start frame meets a given condition.

In accordance with one of some aspect, there is provided an endoscope system comprising:
a memory that stores a trained model;
an endoscopic scope that captures a detection image; and
a processor that accepts the detection image as input, and performs a process of detecting a position of a given object from the detection image by using the trained model,
the trained model having been trained by machine learning based on training data in which annotation data is associated with a frame image in a video,
the annotation data being generated by:
acquiring the video including multiple frames;
setting a start frame to start tracking of a tracking target;
extracting multiple representative points of a contour of the tracking target in the start frame;
tracking the extracted multiple representative points in frames subsequent to the start frame;
performing outlier determination on the tracked multiple representative points based on an interrelationship of the multiple representative points;
performing a process of removing an outlier representative point that is a representative point determined to be an outlier;
updating the representative points by extracting new representative points based on multiple representative points after the process of removing the outlier representative point, in a case where any frame subsequent to the start frame meets a given condition; and
generating the annotation data in which an inside of a closed curve generated based on the tracked multiple representative points is defined as an annotation region for each frame subsequent to the start frame.

In accordance with one of some aspect, there is provided a tracking method comprising:
acquiring a video including multiple frames;
setting a start frame to start tracking of a tracking target;
extracting multiple representative points of a contour of the tracking target in the start frame;
tracking the extracted multiple representative points in frames subsequent to the start frame;
performing outlier determination on the tracked multiple representative points based on an interrelationship of the multiple representative points;
performing a process of removing an outlier representative point that is a representative point determined to be an outlier; and
updating the representative points by extracting new representative points based on multiple representative points after the process of removing the outlier representative point, in a case where any frame subsequent to the start frame meets a given condition.

BRIEF DESCRIPTION OF THE DRAWINGS

FIG. 10 is an example of annotation.

FIGS. 17A and 17B are diagram illustrating scattering of a region due to tracking errors.

DESCRIPTION OF EXEMPLARY EMBODIMENTS

Figure 1:
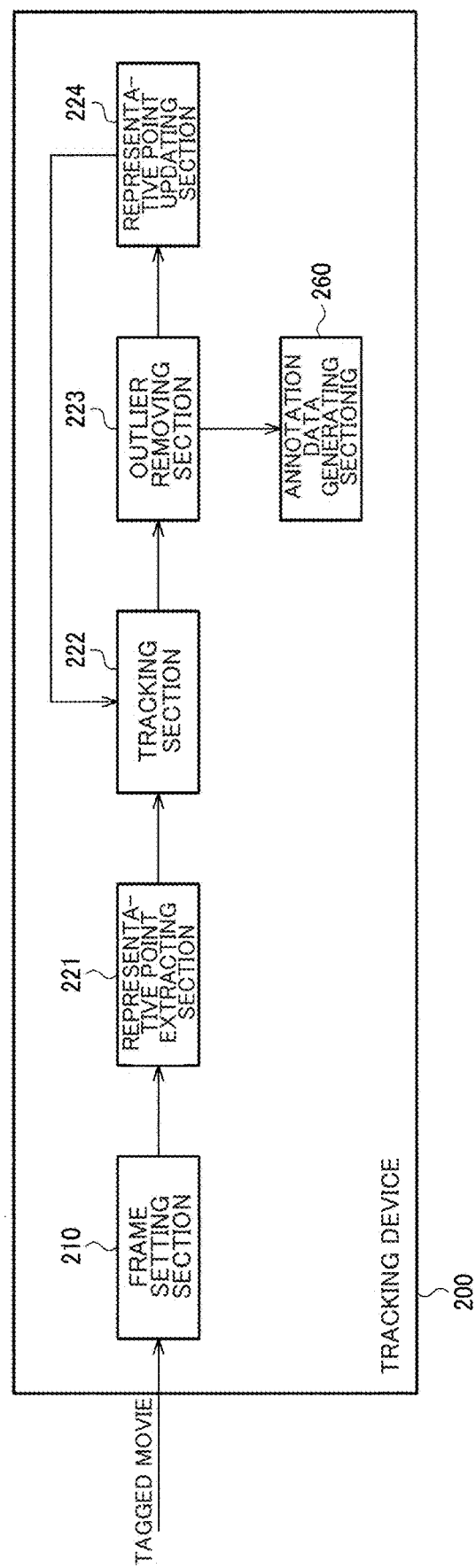
FIG. 1 is a configuration example of a tracking device.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. Overview

Methods for tracking a tracking target in a video are conventionally widely used. For example, implementation of machine learning for recognizing an object in an image requires a large number of images attached with tags. The images attached with the tags are hereinafter referred to as tagged images. Generation of the tagged images needs to be done manually, and thus takes a lot of time. In a case of surgery using an endoscope, as will be described later referring to FIG. 16, tagging needs to be done by a surgeon who is skilled in the surgery, however, tagging a large number of images is not easy.

In order to reduce a load for generating the tagged images, there is a method in which a tag generated in a given frame is tracked to tag a new frame using a tracking result. However, an intended tracking target in the present embodiment is a region including a group of pixels in an image.

FIGS. 17A and 17B are schematic diagrams illustrating a conventional method of region-based tracking. FIG. 17A is a tagged image to which a tag is manually attached, for example. A region corresponding to the tag in the image is hereinafter referred to as a tag region. In the conventional method of the region-based tracking, processing is performed for each pixel. As for an example illustrated in FIG. 17A, tracking is performed for each of a plurality of pixels in the tag region. When the tracking is continued over multiple frames, tracking errors are accumulated as a number of times of tracking increases, or as time passes in a video. FIG. 17B illustrates a result of a predetermined number of times of tracking. As illustrated in FIG. 17B, the tag region that is a single continuous region in an original image may be scattered due to an influence of the tracking errors.

A tracking device 200 according to the present embodiment extracts a contour of a tag region and tracks a contour line of an extraction result as a target. Then, the tracking device performs mask processing to an inside of a contour line of a tracking result to determine a tag region in a new frame. The tracking device 200 may track all points of the contour line, or some points of the contour line. As a result, scattering of the tag region is suppressed, so that the tag region can be appropriately tracked.

However, even when the contour line is tracked, the tracking errors occur. In view of this, according to the present embodiment, an outlier is removed to suppress the influence of the tracking errors. Moreover, according to the present embodiment, when a number of representative points to be tracked decreases by outlier removal, the representative points used for tracking are re-extracted when a predetermined condition is met. With these methods, tracking accuracy can be further enhanced. The methods according to the present embodiment are described in detail below.

2. Tracking Device

FIG. 1 is a diagram illustrating a configuration example of the tracking device 200 according to the present embodiment. As illustrated in FIG. 1, the tracking device 200 includes a frame setting section 210, a representative point extracting section 221, a tracking section 222, an outlier removing section 223, a representative point updating section 224, and an annotation data generating section 260. However, the tracking device 200 is not limited to the configuration illustrated in FIG. 1, and can be implemented in various modified manners, for example, by omitting some of components or adding other components. For example, the annotation data generating section 260 may be omitted.

The tracking device 200 according to the present embodiment includes hardware described below. The hardware may include at least one of a circuit that processes a digital signal and a circuit that processes an analog signal. For example, the hardware may include one or more circuit devices mounted on a circuit board, or one or more circuit elements. The one or more circuit devices are an integrated circuit (IC) or a field programmable gate array (FPGA), for example. The one or more circuit elements are a resistor or a capacitor, for example.

Furthermore, each section of the tracking device 200 including the frame setting section 210, representative point extracting section 221, tracking section 222, outlier removing section 223, representative point updating section 224, and annotation data generating section 260 may be implemented by a processor described below. The tracking device 200 includes a memory that stores information, and a processor that operates based on the information stored in the memory. The information includes, for example, a program and various data. The processor includes hardware. The processor may be any one of various processors such as a central processing unit (CPU), a graphics processing unit (GPU), or a digital signal processor (DSP). The memory may be a semiconductor memory such as a static random access memory (SRAM) or a dynamic random access memory (DRAM), a register, a magnetic storage device such as a hard disk drive, or an optical storage device such as an optical disc device. For example, the memory stores a computer-readable instruction. A function of each of the sections of the tracking device 200 is implemented as a process when the processor executes the instruction. The instruction used here may be an instruction set that is included in a program, or may be an instruction that instructs a hardware circuit included in the processor to operate. Furthermore, all or part of the frame setting section 210, representative point extracting section 221, tracking section 222, outlier removing section 223, representative point updating section 224, and annotation data generating section 260 may be implemented by cloud computing, so that a video is acquired through a network and a tracking process described later is performed on the cloud computing.

The frame setting section 210 acquires a video and sets a start frame to start tracking. The video used here is a tagged video including some tagged frames, for example.

The representative point extracting section 221 extracts representative points used for tracking from a contour of a tracking target in the start frame. The contour of the tracking target in the start frame can be obtained from a tagged region in the start frame.

The tracking section 222 tracks the representative points extracted by the representative point extracting section 221 in frames subsequent to the start frame. As will be described later, when the representative points are updated by the representative point updating section 224, the tracking section 222 tracks the updated representative points.

The outlier removing section 223 performs outlier determination mutually among the representative points tracked by the tracking section 222, and a process of removing an outlier representative point determined to be an outlier.

The representative point updating section 224 determines whether the representative points need to be updated. When the representative point updating section 224 determines that the representative points need to be updated, the representative point updating section 224 extracts new representative points based on a state of remaining representative points in a frame of a processing target after the outlier representative point is removed.

The annotation data generating section 260 performs a process of generating annotation data based on a tracking result for each frame subsequent to the start frame. The annotation data is data in which an inside of a closed curve connecting the tracked representative points is defined as an annotation region, and is metadata provided to an associated frame image. Data including a frame image and annotation data provided to the frame image is used as training data for machine learning, for example.

Figure 2:
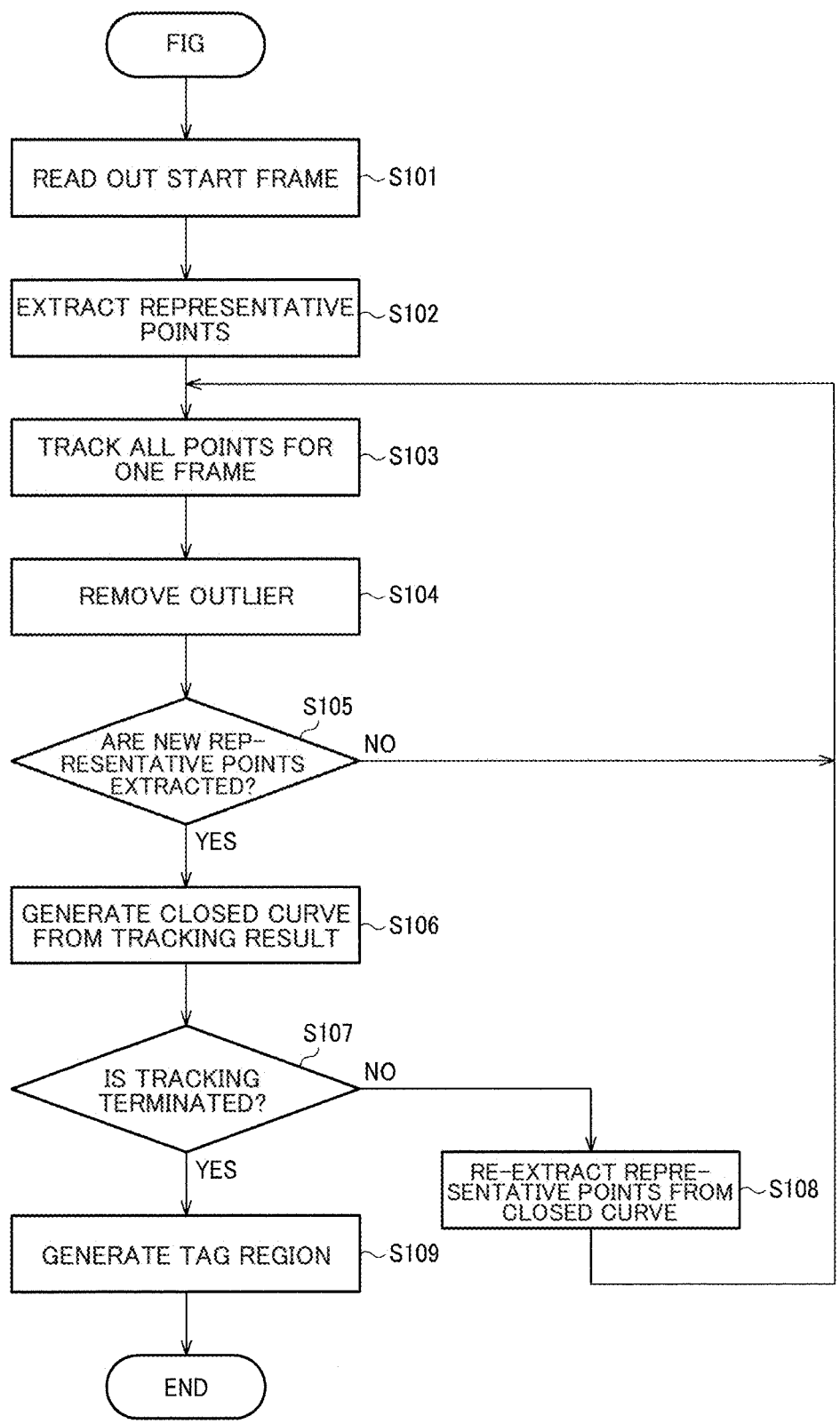
FIG. 2 is a flowchart illustrating processing procedures performed by the tracking device.

FIG. 2 is a flowchart illustrating a process according to the present embodiment. When this process starts, the frame setting section 210 sets a tagged frame as a start frame in a step S101. The frame setting section 210 may automatically set a first frame of a video as the start frame for tracking.

Figure 3:
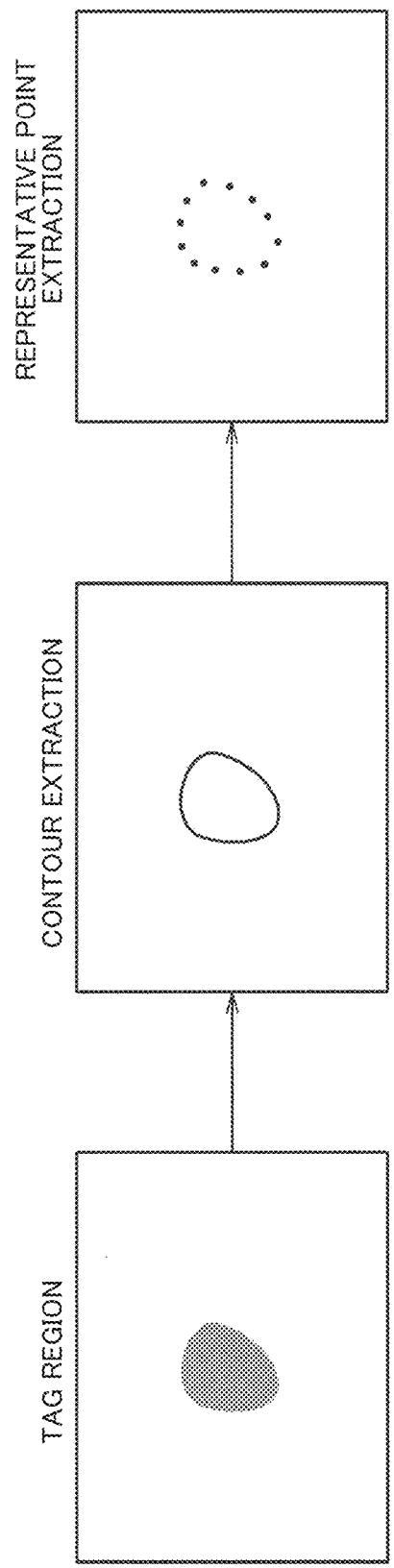
FIG. 3 is a diagram illustrating a process of extracting representative points based on a tag region.

Next, in a step S102, the representative point extracting section 221 extracts representative points to be tracked from a contour of a tracking target included in the start frame. FIG. 3 is a diagram illustrating an extraction process of the representative points. The tag according to the present embodiment is information input by an operator such as a surgeon, and is the annotation data provided to an image as the metadata, as will be described later referring to FIGS. 10 and 11, for example. The annotation data is a mask image including a tag region set with a first pixel value and a region other than the tag region set with a second pixel value different from the first pixel value, for example.

The representative point extracting section 221 extracts a contour of the tag region. When information about the tag region is acquired as the mask image as described above, the representative point extracting section 221 extracts pixels with the first pixel value that are adjacent to pixels with the second pixel value as the contour of the tag region, for example. However, an extraction process of the contour may be implemented in various modified manners, for example, by using a known edge extraction filter.

The representative point extracting section 221 may select all pixels on the contour as the representative points used for tracking. Also in this case, the tracking target does not need to include pixels inside the tag region. Accordingly, scattering of the region can be suppressed, and a processing load can be reduced. The representative point extracting section 221 may also extract some pixels on the contour as the representative points. For example, the representative point extracting section 221 extracts the representative points from the pixels on the contour at a regular interval. For example, the representative point extracting section 221 extracts twelve representative points such that intervals between adjacent representative points are the same (approximately the same included) as illustrated in FIG. 3. A number n (n is an integer of two or more) of representative points to be extracted may be set in advance, and the representative point extracting section 221 may divide the contour line into n to set n representative points. Alternatively, the interval between adjacent representative points may be set in advance, and the representative point extracting section 221 may set the representative points according to the interval. In this case, the number of representative points changes depending on a length of the contour line.

Figure 7:
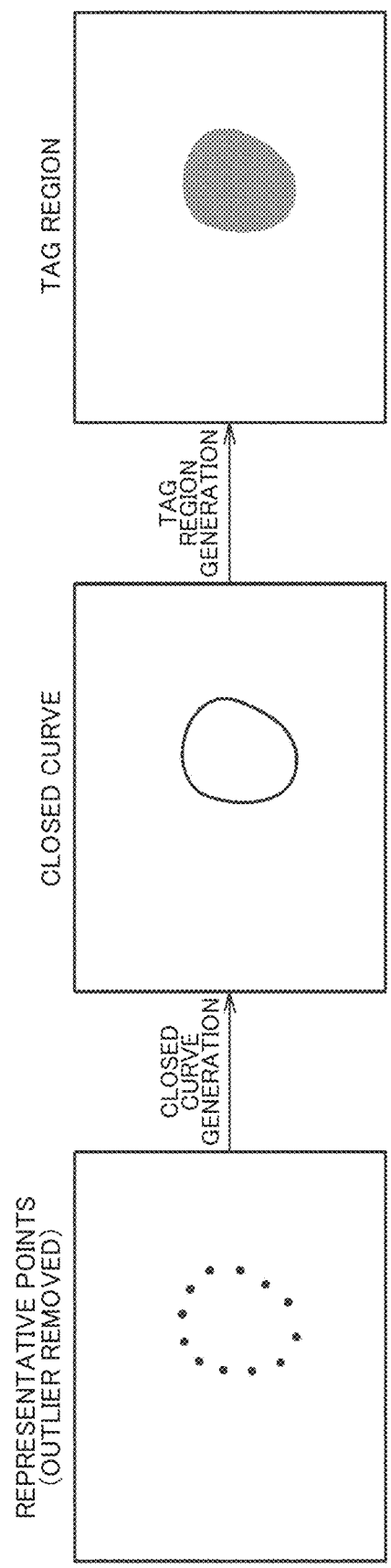
FIG. 7 is a diagram illustrating a process of generating the tag region based on the representative points.

As will be described later referring to FIG. 7, the tracking device 200 according to the present embodiment generates a closed curve connecting the representative points of the tracking result, and defines the inside of the closed curve as the tag region. Therefore, the representative points used for tracking need to be points that can reproduce the contour of the tracking target with rather high accuracy when the representative points are connected. With a contour of a simple shape, information about the contour is unlikely to be lost even when the number of representative points is small. On the contrary, with a contour of a complicated shape, the information about the contour may be lost unless many representative points are set.

The representative point extracting section 221 may set the representative points based on a curvature of the contour. For example, the representative point extracting section 221 divides the extracted contour into multiple curves, and obtains the curvature of each of the divided curves. For example, assuming that a curve is approximated by a circle, a radius of the circle is a curvature radius, and a reciprocal of the curvature radius is a curvature. The curvature of the contour may be obtained for each pixel. The representative point extracting section 221 extracts more representative points from a portion with a large curvature of the contour than from a portion with a small curvature. As a result, a density of the representative points can be regulated according to the shape of the contour, and thus the contour can be appropriately reproduced based on the representative points. That is, the region of the tracking target can be tracked with high accuracy.

After the representative points are extracted in the start frame, the tracking section 222 tracks the extracted representative points in a step S103. Specifically, the tracking section 222 infers at which position in an image in a subsequent second frame a given representative point in a first frame is present.

Figure 4:
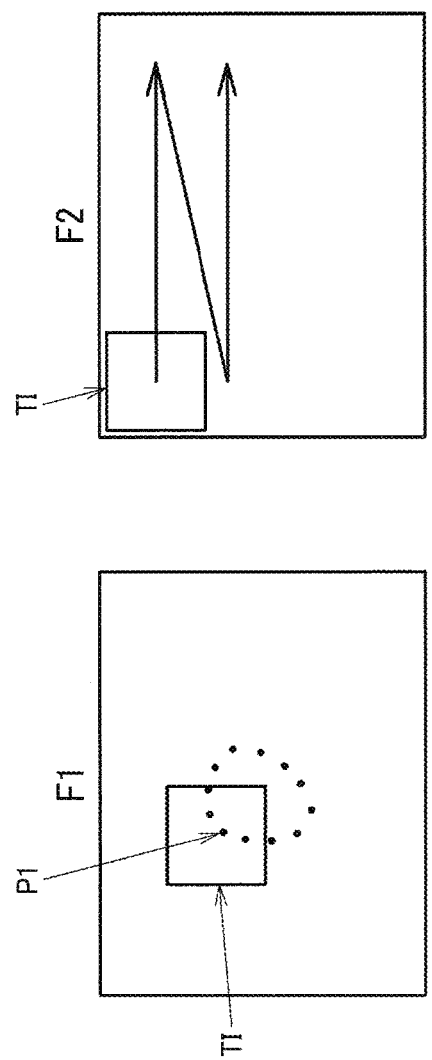
FIG. 4 is a diagram illustrating a tracking process.

FIG. 4 is a diagram illustrating a tracking process. The tracking is performed using frame images in two frames. The tracking section 222 extracts a region in a vicinity of a given representative point P1 as a template image TI from a frame image F1 in the first frame. For example, the template image TI is a square image in a predetermined size having the representative point P1 as its center, however, the size and the shape may be implemented in various modified manners. The tracking section 222 performs template matching using the template image TI in a frame image F2 in the second frame as illustrated in FIG. 4. Then, the tracking section 222 determines a position with a lowest difference degree or a position with a highest matching degree with respect to the template image TI as a point corresponding to the representative point P1. A detection range for the template matching may include the entire frame image F2 or part of the frame image F2. The tracking section 222 performs the process illustrated in FIG. 4 for each of the representative points in the first frame to track the representative points. A tracking method may be implemented in various modified manners, such as a tracking method based on luminance or contrast of a frame image at a representative point, or a tracking method by an optical flow.

Next, in a step S104, the outlier removing section 223 performs outlier removal from points after tracking. The representative points according to the present embodiment are points representing the contour of the tracking target. A significant change in shape of the tracking target in the image is unlikely to happen in one frame. A target to be imaged significantly changes when a scene change occurs, as will be described later referring to FIG. 12, for example. In such a case, continuation of the tracking is unlikely to be needed. That is, in a scene where the tracking is performed, moving tendencies of multiple representative points have similarity to some extent. When a given representative point obviously moves differently from other representative points, the tracking of the given representative point is likely to be an error.

The outlier removing section 223 extracts a representative point that moves differently from other representative points as an outlier representative point based on an interrelationship of the representative points. For example, the outlier removing section 223 determines that the given representative point is the outlier representative point when a difference between a moving distance of the given representative point and a moving distance of at least one adjacent representative point exceeds a predetermined value. Alternatively, the outlier removing section 223 determines that the given representative point is the outlier representative point when a distance between the given representative point and at least one adjacent representative point exceeds a predetermined value.

Alternatively, the outlier removing section 223 obtains a curvature of a curve formed by the given representative point and adjacent representative points, and determines that the given representative point is the outlier representative point when the obtained curvature exceeds a predetermined value. The adjacent representative points used here are two representative points adjacent to the given representative point in a direction along the contour line, i.e., the representative points on both sides of the given representative point. However, the adjacent representative points may be implemented in various modified manners, for example, by adding a representative point other than the adjacent two representative points. As a result, determination of a deviation degree of the representative point enables appropriate removal of the outlier representative point.

Figure 5:
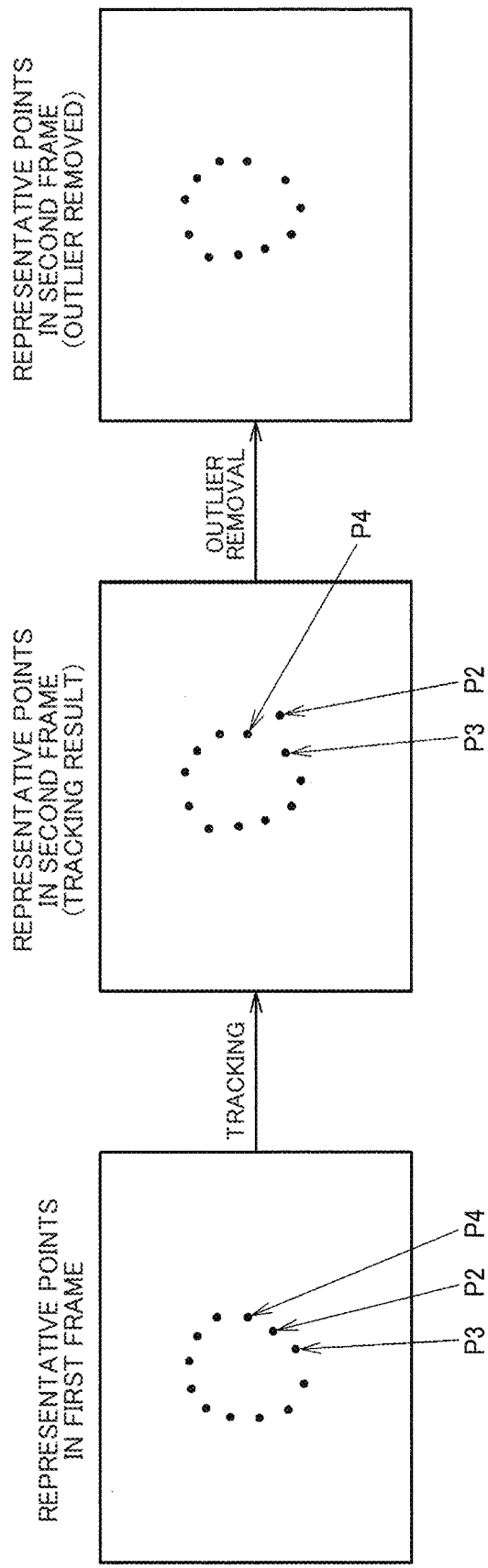
FIG. 5 is a diagram illustrating a process of removing an outlier representative point.

FIG. 5 is a diagram illustrating an outlier removal process. A moving distance of a representative point indicated by P2 in FIG. 5 is larger than moving distances of representative points P3 and P4 adjacent to the representative point P2. Alternatively, as for a curve passing through the representative points P2 to P4, the curvature of the curve is large. The curvature may be compared with a given fixed value, a curvature in the first frame, or a curvature of another representative point in the second frame. In any case, the curvature corresponding to the representative point P2 is determined to be large. Accordingly, the outlier removing section 223 removes the representative point P2.

As a result of processing in the steps S103 and S104, representative points excluding the inappropriate representative point can be acquired with high accuracy in the second frame subsequent to the first frame of a tracking source. The tracking process illustrated in FIG. 4 is performed for each of the multiple representative points after the outlier removal in the second frame, so that the tracking can be continued in a third frame subsequent to the second frame and after. The outlier removal process may be performed for each frame, or for every series of tracking in a predetermined multiple number of frames.

However, according to the present embodiment, the representative point updating section 224 determines whether the representative points need to be updated in a step S105 in order to perform the tracking with accuracy. As described above, in the method according to the present embodiment, the representative point determined to be the outlier representative point is removed, and the number of representative points may decrease. When the number of remaining representative points becomes excessively small, reproducing the contour of the tracking target with the remaining representative points is difficult. As a result, tracking accuracy is degraded. In view of this, the representative point updating section 224 determines that the representative points need to be updated when the number of representative points becomes smaller than a predetermined number.

Figure 6:
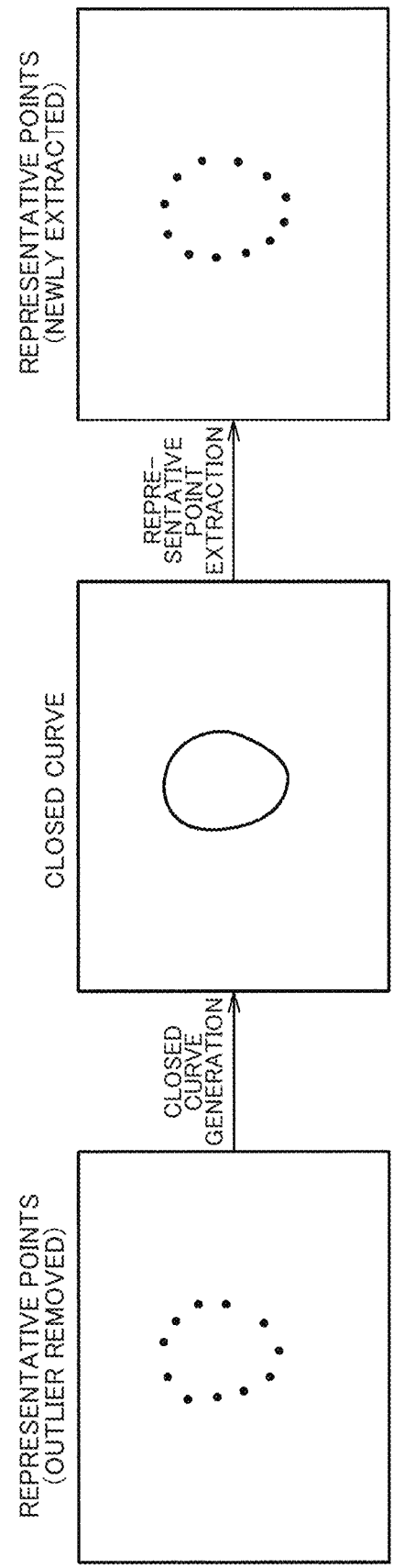
FIG. 6 is a diagram illustrating a process of updating the representative points.

FIG. 6 is a diagram illustrating an update process of the representative points. In a step S106, the representative point updating section 224 first connects an all point group of the remaining representative points after the outlier removal to generate a closed curve. The representative point updating section 224 performs known spline interpolation to generate the closed curve, for example. However, there are various known methods for generating a closed curve with multiple points, and these methods are widely applicable to the present embodiment.

Next, in a step S108, the representative point updating section 224 re-extracts representative points from the generated closed curve. Meanwhile, a purpose of the update process of the representative points is to continue the tracking with accuracy. Thus, in the flowchart in FIG. 2, whether to terminate the tracking is first determined in a step S107, and then re-extraction of the representative points is performed when the tracking is not terminated.

A re-extraction process of the representative points is the same as the extraction process of the representative points from the contour in the start frame. That is, the representative point updating section 224 may extract the representative points from pixels on the closed curve at a regular interval, or may change the density of the representative points according to the curvature of the closed curve. At this time, the representative points to be newly extracted do not need to coincide with original representative points. For example, when the closed curve is generated from eleven representative points and twelve representative points are re-extracted as illustrated in FIG. 6, it is not necessary to keep the original eleven representative points to add one representative point. All the twelve representative points may be newly selected. This is because the method according to the present embodiment is for tracking the contour of the tracking target, and not for considering positions of the representative points on the contour.

The representative point updating section 224 may determine that the representative points need to be updated when reliability of a tracking result becomes lower than a predetermined value. The reliability of the tracking result is, for example, a lowest value of the difference degree or a highest value of the matching degree of the template matching. The difference degree is a sum of squared difference (SSD), or a sum of absolute difference (SAD), for example. The reliability is determined to be low when the lowest value is equal to or higher than a predetermined threshold value. The matching degree is a normalized cross correlation (NCC), for example. The reliability is determined to be low when the highest value is equal to or lower than a predetermined threshold value. The update of the representative points can update the template image for the template matching. As a result, the update of the representative points can enhance tracking accuracy.

Considering that the representative points are refreshed when the tracking accuracy is degraded, the representative point updating section 224 may determine that the representative points need to be updated when the tracking is performed in a predetermined number of frames, i.e., when given time passes. When the tracking is continued over multiple frames, tracking errors are accumulated. By setting passage of the given time as a determination condition, the representative points can be updated when the tracking accuracy is likely to be degraded.

When the representative points do not need to be updated (No in the step S105), or after the update of the representative points (after processing in the step S108), the process returns to the step S103 to continue. The tracking section 222 performs the tracking for one frame based on the representative points in a latest frame. Processing after that is the same, i.e., the outlier removal process is performed, the update process of the representative points is performed as needed, and the tracking is performed in a subsequent frame based on the results of the processes.

When the tracking is determined to be terminated (Yes in the step S107), the tracking device 200 performs a generation process of a tag region in a step S109. FIG. 7 is a diagram illustrating the generation process of the tag region. Specifically, a closed curve connecting the representative points is generated in each frame, and a process of generating the annotation data in which the inside of the closed curve is defined as the tag region is performed. The generation process of the closed curve is the same as the process in the step S106. The representative points in each frame are the representative points after the removal process of the outlier representative points. As for a frame applied with the update process of the representative points, the closed curve of a processing result in the step S106 may be used.

The tag region according to the present embodiment may be the metadata (annotation data) provided to the image. In this case, the process illustrated in FIG. 7 is performed by the annotation data generating section 260. The annotation data generated by the annotation data generating section 260 is a mask image for identifying the tag region, for example.

As described above, the tracking device 200 according to the present embodiment includes the frame setting section 210, the representative point extracting section 221, the tracking section 222, the outlier removing section 223, and the representative point updating section 224. The frame setting section 210 sets the start frame to start the tracking of the tracking target in the video including the multiple frames. The representative point extracting section 221 extracts the multiple representative points of the contour of the tracking target in the start frame. The tracking section 222 tracks the extracted multiple representative points in the frames subsequent to the start frame. The outlier removing section 223 performs the outlier determination on the multiple representative points, tracked by the tracking section 222, based on the interrelationship of the multiple representative points, and removes the outlier representative point that is the representative point determined to be the outlier. The representative point updating section 224 updates the representative points by extracting new representative points based on the multiple representative points after the process of removing the outlier representative point when any frame subsequent to the start frame meets a given condition.

According to the method in the present embodiment, the representative points are extracted from the contour, and the tracking is performed based on the representative points. Tracking the contour can suppress occurrence of variation of pixels. As a result, the region-based tracking can be appropriately performed. Furthermore, since the tracking of the pixels inside the region can be omitted, high-speed processing can be implemented. At this time, the outlier determination is performed to remove the inappropriate representative point from the tracking result, so that the tracking accuracy can be enhanced. Since the representative points are all set on the contour, the outlier representative points can be appropriately detected using the interrelationship of the representative points. Furthermore, since the representative points are updated, the tracking can be implemented with accuracy even when the outlier representative point is removed. Specifically, updating the representative points enables implementation of an identifying process of the contour of the tracking target from the representative points with high accuracy.

Furthermore, the representative point extracting section 221 may set a tag region, which is a region tagged to the start frame, as the tracking target. The representative point extracting section 221 extracts multiple representative points of a contour of the tag region. As a result, the tracking can be appropriately performed with the tag region as the target. The region to be tagged may be an object whose position and shape are not clearly captured in the image, as will be described later referring to FIGS. 8A to 8C. Tagging such an object is not easy unless it is performed by an expert. However, it can be efficiently performed by tracking.

Furthermore, the representative point extracting section 221 may extract the multiple representative points such that adjacent representative points are spaced apart at a given interval on the contour of the tracking target. As a result, the representative points can be efficiently set.

Furthermore, the representative point extracting section 221 may extract the multiple representative points such that, on the contour of the tracking target, a density of representative points at a portion with a large curvature of the contour is higher than a density of representative points at a portion with a small curvature of the contour. The density used here is a number of representative points set for each unit length of the contour. Accordingly, the representative points can be set by taking the shape of the contour in consideration. As a result, the contour of the tracking target can be appropriately reproduced based on the representative points.

Furthermore, the outlier removing section 223 may determine a deviation degree of a first representative point of the multiple representative points based on the first representative point and one or more adjacent representative points adjacent in a direction along the contour so as to determine whether the first representative point is the outlier representative point. Specifically, the outlier removing section 223 determines the deviation degree of the first representative point based on relative distance information between the first representative point and the one or more adjacent representative points. The relative distance information may be information about a distance between the first representative point and at least one adjacent representative point.

Alternatively, the relative distance information may be information about a relationship between a moving distance of the first representative point between frames and a moving distance of at least one adjacent representative point between the frames. Furthermore, the outlier removing section 223 determines the deviation degree of the first representative point based on a curvature of a curve formed by the first representative point and multiple adjacent representative points. As a result, a representative point that is highly likely to be an error in tracking can be removed as the outlier representative point based on a relative relationship between a given representative point and one or more surrounding representative points.

Furthermore, the representative point updating section 224 extracts new representative points based on remaining multiple representative points after the process of removing the outlier representative point, when the number of representative points becomes equal to or smaller than a given number threshold value due to the process of removing the outlier representative point. When the outlier representative point is removed, processing accuracy can be enhanced from a viewpoint of removing the inappropriate representative point from the processing. However, this decreases the number of representative points. When the number of representative points excessively decreases, reproducing the contour of the tracking target based on the representative points is difficult. As a result, tracking accuracy is degraded. According to the method in the present embodiment, the representative points can be updated while an enough number of representative points remain to reproduce the contour with sufficient accuracy. This can suppress degradation of accuracy due to outlier removal. In other words, combined with the update process of the representative points, the outlier removal process can appropriately contribute to accuracy enhancement.

Furthermore, the representative point updating section 224 may extract the new representative points based on the multiple representative points after the process of removing the outlier representative point, when the reliability of the tracking result is equal to or lower than a given reliability threshold value. Alternatively, the representative point updating section 224 may extract the new representative points based on the multiple representative points after the process of removing the outlier representative point at a given time interval. As a result, since the representative points are refreshed when the tracking accuracy may be degraded, the tracking accuracy can be enhanced.

Furthermore, the representative point updating section 224 may generate a closed curve based on the multiple representative points after the process of removing the outlier representative point, and extract the new representative points from the generated closed curve. With such a closed curve, the new representative points also become points corresponding to the contour of the tracking target. As a result, the region of the tracking target can be tracked appropriately even when the representative points are updated.

Furthermore, the tracking device 200 may include the annotation data generating section 260. The annotation data generating section 260 generates the annotation data that the inside of the closed curve generated based on the tracked multiple representative points is defined as the annotation region for each frame subsequent to the start frame. More specifically, the annotation data generating section 260 generates the annotation data in which the inside of the closed curve generated based on the multiple representative points after the process of removing the outlier representative point is defined as the annotation region. As a result, the annotation data generating section 260 can provide the metadata capable of identifying the region of the tracking target to each frame of the video. The annotation data is used as training data for machine learning as described later, for example.

Furthermore, the processes performed by the tracking device 200 according to the present embodiment may be implemented as a tracking method. The tracking method includes steps of acquiring the video including the multiple frames, setting the start frame to start the tracking of the tracking target, extracting the multiple representative points of the contour of the tracking target in the start frame, tracking the extracted multiple representative points in the frames subsequent to the start frame, performing the outlier determination based on the interrelationship of the tracked multiple representative points, removing the outlier representative point that is the representative point determined to be the outlier, and updating the representative points by extracting the new representative points based on the multiple representative points after the process of removing the outlier representative point when any frame subsequent to the start frame meets the given condition.

3. Endoscope System, Learning Device, and Trained Model

Output of the tracking device 200 described above may be used for machine learning. For example, in an endoscopic surgery, an operator may have difficulty to recognize an object whose position and shape are not clearly displayed in an image. For example, the operator follows procedures using a predetermined landmark as a guide in the endoscopic surgery, however, a position and shape of the landmark may not be clearly displayed in the image. At this time, an inexperienced surgeon may not be able to recognize this indistinct landmark. The position and shape are a position and a shape.

Figure 8A:
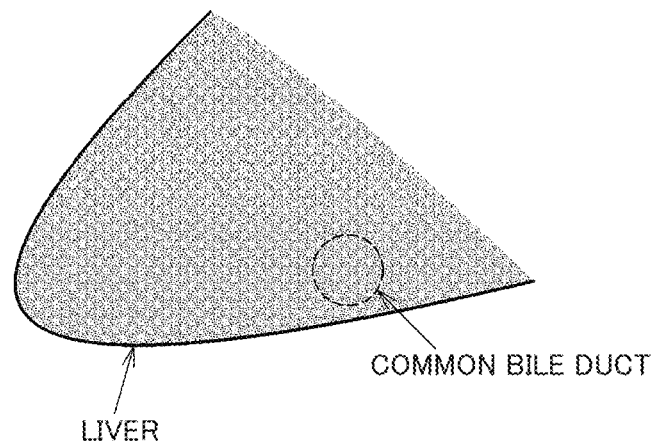
FIGS. 8A to 8C are examples of objects whose positions and shapes are not clearly displayed in images.
Figure 8B:
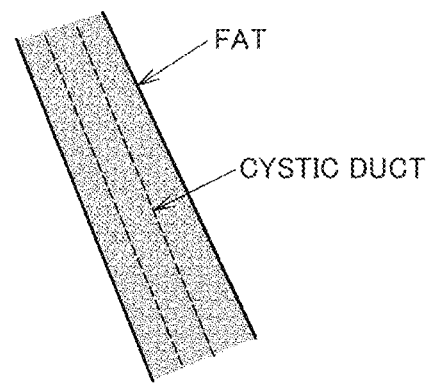
Figure 8C:
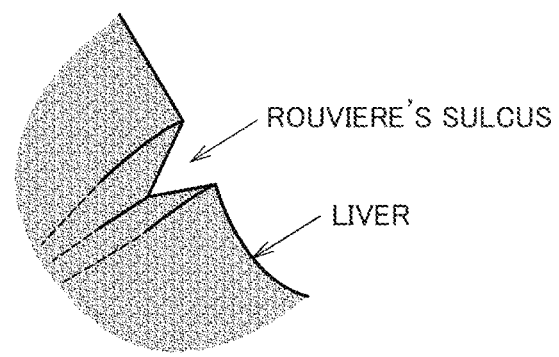

FIGS. 8A to 8C illustrate examples of objects whose positions and shapes are not clearly displayed in images. The objects in FIGS. 8A, 8B, and 8C are a common bile duct, a cystic duct, and a Rouviere's sulcus, respectively. FIGS. 8A to 8C are schematic diagrams and do not show accurate shapes of an actual organ or tissue. The same applies to FIG. 10 and after.

FIGS. 8A and 8B illustrate examples of a state where the object is covered with the organ or tissue. In this case, even when the object is in an angle of view, the object itself is not displayed in the image, or the position and shape of the object are not clear. FIG. 8C illustrates an example of a state where the object is exposed in the image and visually recognizable, but a boundary of the object is not distinct. As illustrated in FIG. 8C, in an endoscope image of laparoscopic cholecystectomy, the Rouviere's sulcus is visually recognizable and a start portion of the sulcus is comparatively distinct. However, the sulcus gradually disappears toward an end portion of the sulcus, and the boundary of the Rouviere's sulcus becomes indistinct.

The common bile duct, cystic duct, and Rouviere's sulcus, and an S4 inferior border described later are the landmarks in the laparoscopic cholecystectomy. The landmark is a guide used for following the procedures of the surgery. According to the present embodiment, these landmarks are annotated as the objects to generate the training data, and the training data is used for machine learning.

Figure 9:
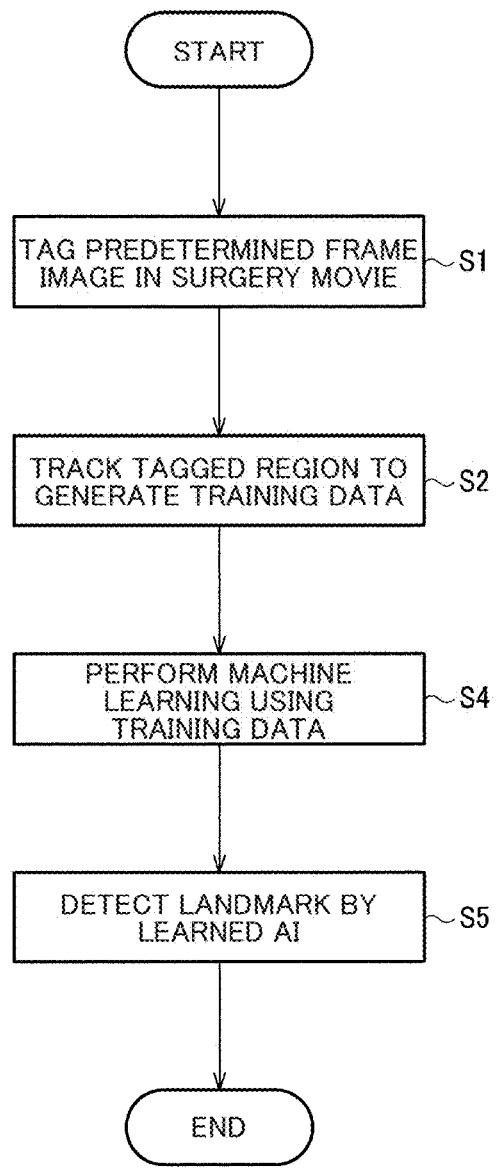
FIG. 9 is a flowchart illustrating a series of procedures from training data generation to object detection.

FIG. 9 is a flowchart illustrating a series of procedures from generation of the training data to detection of the object according to the present embodiment.

Steps S1 and S2 are steps for generating the training data. In the step S1, an operator tags a predetermined frame image in a surgery video. The operator is a surgeon skilled in a target surgery, for example. As will be described later, the predetermined frame image is a first frame image after a scene change in the video. Next, in the step S2, the tracking device 200 tracks a tagged region to generate the training data. Details of the tracking method are as described above. Each frame image tagged in the steps S1 and S2 in the surgery video is the training image. Tagging an image is referred to as annotation.

A step S4 is a learning step. That is, a learning device performs machine learning using the training data generated in the steps S1 and S2. A trained model obtained by this machine learning is stored in a storage section 7 of an information processing system 10 described later.

A step S5 is a step for inferring by learned artificial intelligence (AI). That is, a processing section 4 of the information processing system 10 detects an object from a detection image based on the trained model stored in the storage section 7. The processing section 4 displays information about the detected object on the detection image.

Next, a method for generating the training data is described. In order to generate the training data, the annotation indicating the position and shape of the object is attached to the training image including the object whose position and shape are not clearly displayed in the image in an angle of view. "Whose position and shape are not clearly displayed in the image" means a state that the position and shape of the object can not be identified by a method for detecting the boundary based on the luminance or contrast.

As for the landmarks whose positions and shapes are not clearly displayed in the image, described above, an operator identifies the positions and shapes in the image based on tacit knowledge to provide the positions and shapes as the annotation data. The operator who performs the annotation is a surgeon who has plenty of tacit knowledge of the laparoscopic cholecystectomy, for example.

FIG. 10 illustrates an example of the annotation. A training image before the annotation includes a liver KZ, a gallbladder TNN, and treatment tools TL1 and TL2. An angle of view of this training image includes a common bile duct, a cystic duct, a Rouviere's sulcus, and an S4 inferior border. In FIG. 10, solid lines in a right lobe of the liver represent a start portion (a comparatively distinct portion) of the Rouviere's sulcus, and broken lines represent a state where the Rouviere's sulcus gradually disappears toward an end portion of the sulcus. A broken line near a lower edge inside a left lobe of the liver represents a region of the S4 inferior border that is an object visually recognizable in the image, but having an indistinct boundary.

The operator performing the annotation identifies the common bile duct, cystic duct, Rouviere's sulcus, and S4 inferior border from the training image and tags each of them. The training image after the annotation is attached with a tag TGA representing the common bile duct, a tag TGB representing the cystic duct, a tag TGC representing the Rouviere's sulcus, and a tag TGD representing the S4 inferior border. For example, the operator specifies a region of the common bile duct and so on using a pointing device such as a mouse or a touch panel. The learning device tags the region specified by the operator in the training image.

Figure 11:
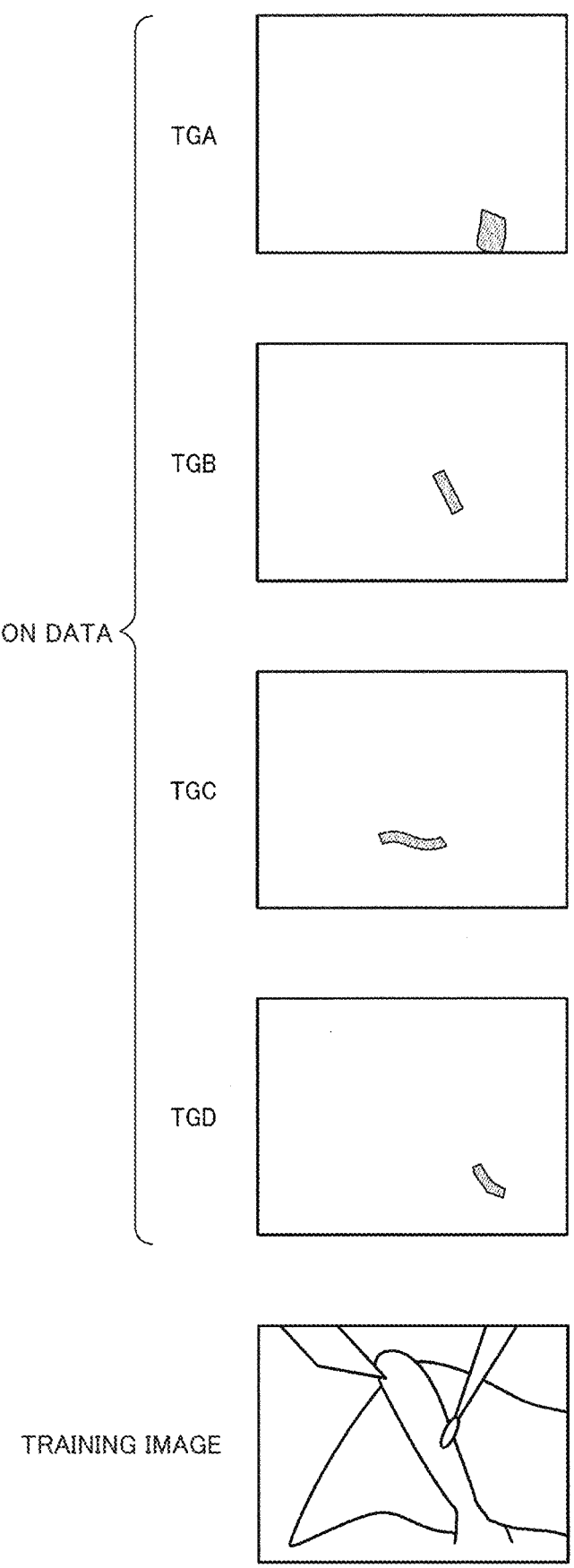
FIG. 11 is an example of training data generated by the annotation.

FIG. 11 illustrates an example of the training data generated by the annotation. As illustrated in FIG. 11, flags are set to pixels in the tagged regions. Map data including flagged pixels is hereinafter referred to as flag data (annotation data). The flag data is generated for each of the tags TGA to TGD. That is, the training data includes the training image and four layers of the flag data generated by tagging the training image.

Figure 12:
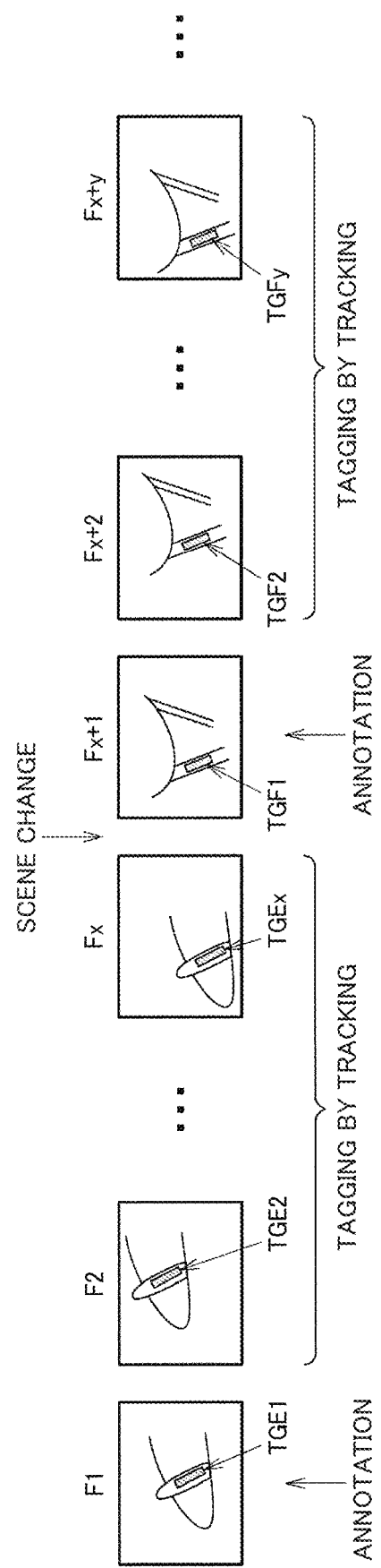
FIG. 12 is a diagram illustrating automatic tagging by tracking.

FIG. 12 is a diagram illustrating automatic tagging by tracking. FIG. 12 illustrates frame images of a video captured by an endoscopic scope 2. Each of the frame images is the training image. Predetermined frame images F1 and Fx+1 are selected from the video. x is an integer of one or more. The predetermined frame images F1 and Fx+1 may be selected by the operator, or by the learning device through scene detection by image processing, for example. The operator tags the selected predetermined frame images F1 and Fx+1.

The predetermined frame images F1 and Fx+1 are frame images when a surgical procedure changes, when brightness of the video changes, when deviation between frames largely changes, or when an object to be imaged changes, for example.

Frame images subsequent to the tagged predetermined frame images are tagged by tracking. Assume that the operator tags the frame image F1 with a tag TGE1. Assuming that a scene change occurs between a frame image Fx and the frame image Fx+1, frame images F2 to Fx are targets to be tagged by tracking. For example, between the frame image F1 and the frame image F2, the tag TGE1 is tracked to acquire a tag TGE2 for the frame image F2. Specifically, as described above, the tag TGE2 is acquired by the respective processes such as extraction of the representative points, tracking of the representative points, outlier removal, generation of the closed curve, and generation of the tag region. Similarly, tags TGE3 to TGEx are generated for frame images F3 to Fx.

Similarly, assume that the operator tags the frame image Fx+1 after the scene change with a tag TGF1. Similarly as above, tags TGF2 to TGFy are attached to frame images Fx+2 to Fx+y by tracking. y is an integer of one or more.

Figure 13:
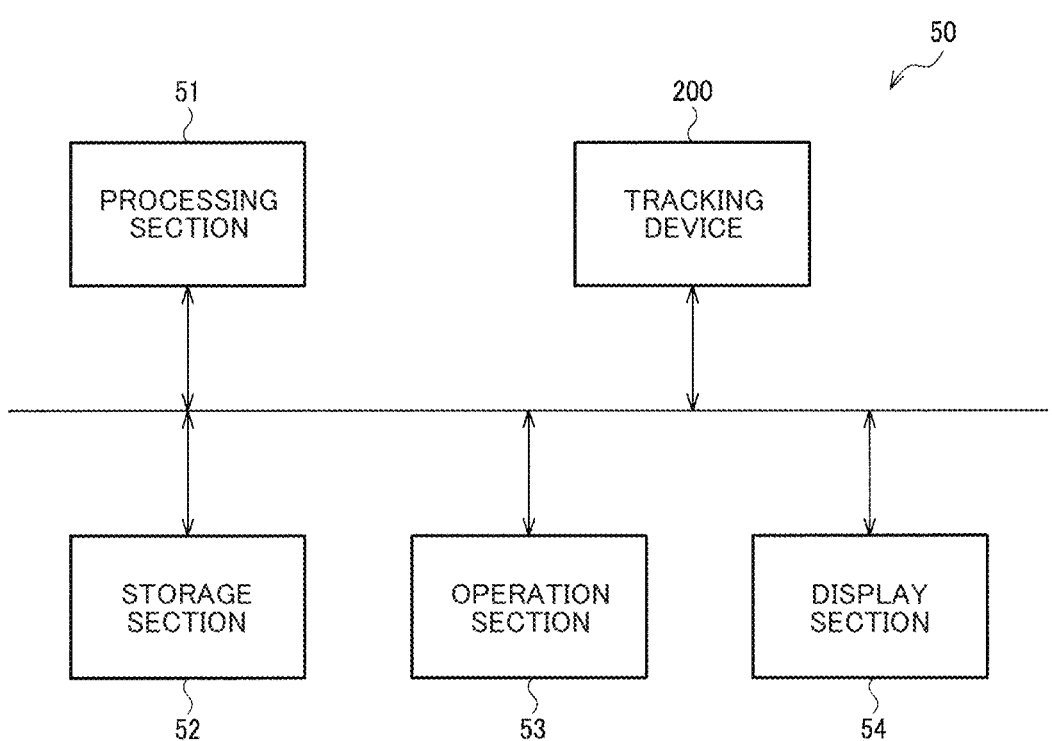
FIG. 13 is a configuration example of a learning device.

FIG. 13 is a configuration example of a learning device 50. The learning device 50 includes the tracking device 200, a processing section 51, a storage section 52, an operation section 53, and a display section 54. For example, the learning device 50 is an information processing device such as a personal computer (PC). The processing section 51 is a processor such as a CPU. The processing section 51 performs the machine learning of a training model to generate a trained model. The storage section 52 is a storage device such as a semiconductor memory, or a hard disk drive. The operation section 53 includes various operation input devices such as a mouse, a touch panel, or a keyboard. The display section 54 is a display device such as a liquid crystal display. Although FIG. 13 illustrates an example that the learning device 50 includes the tracking device 200, the learning device 50 and the tracking device 200 may be separate devices.

Figure 14:
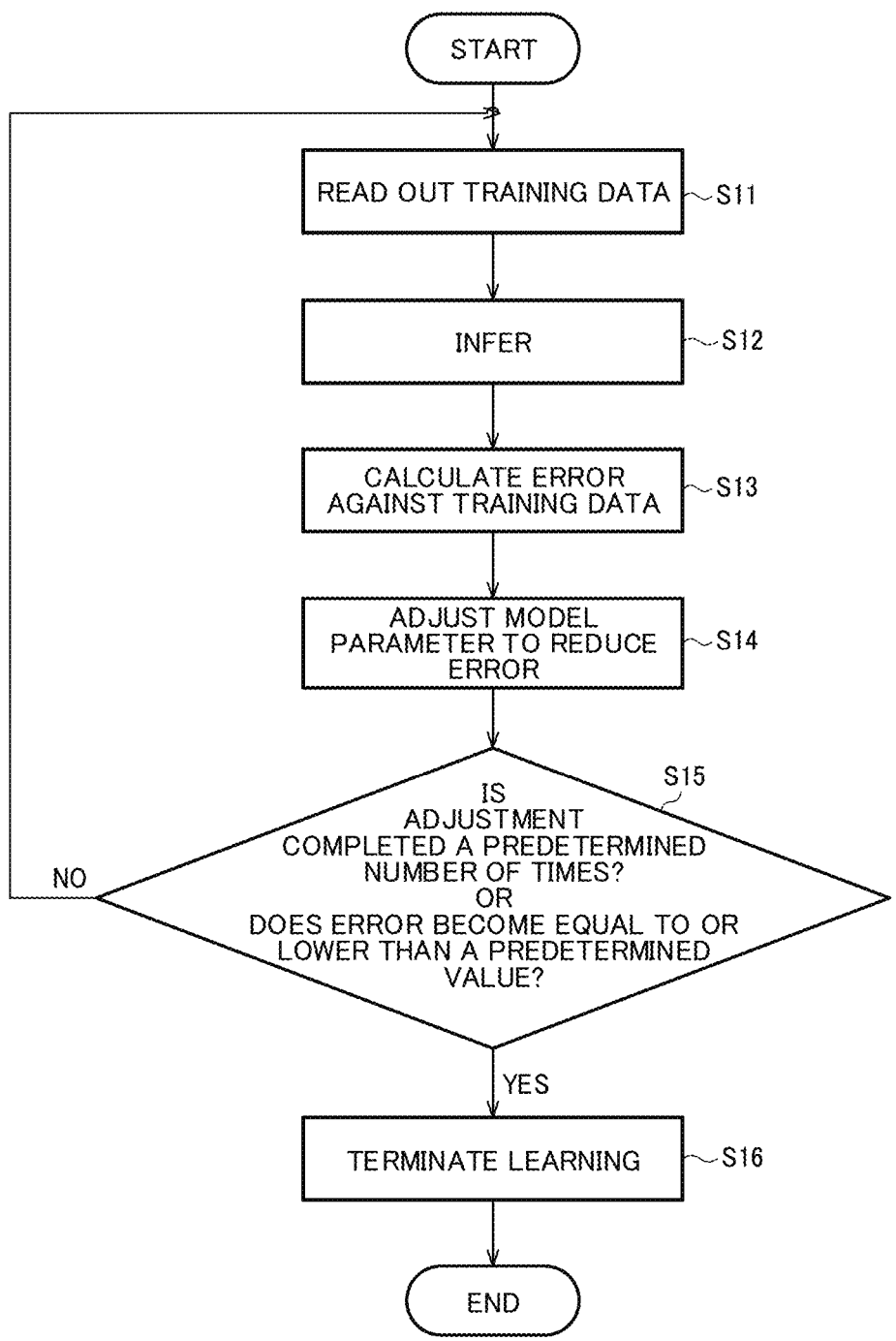
FIG. 14 is a flowchart illustrating learning procedures.

FIG. 14 is a flowchart illustrating learning procedures. The annotation data generated by the tracking device 200 is associated with the training image and is stored in the storage section 52 as the training data.

Figure 15:
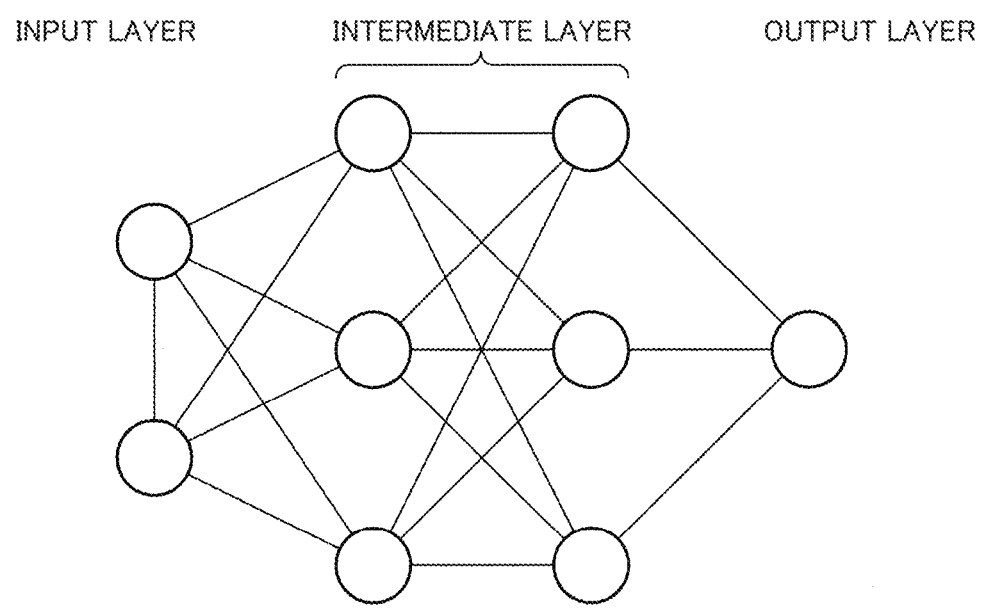
FIG. 15 is an example of a neural network.

The machine learning according to the present embodiment may use a neural network. FIG. 15 is a schematic diagram illustrating the neural network. The neural network includes an input layer that accepts input data, an intermediate layer that calculates based on output from the input layer, and an output layer that outputs data based on output from the intermediate layer. FIG. 15 illustrates an example of a network including two intermediate layers, however, a number of intermediate layers may be one, or three or more. In addition, a number of nodes (neurons) included in each layer is not limited to a number in the example illustrated in FIG. 15, and can be modified in various manners. In view of accuracy, it is preferable to perform deep-layered learning (deep learning) using a neural network including multiple layers in the present embodiment. The multiple layers used here means four layers or more in a narrow sense.

As illustrated in FIG. 15, nodes included in a given layer are connected to nodes in an adjacent layer. Each connection is set with a weight. Each node multiplies output from previous nodes by the weights to obtain a total value of multiplication results. In addition, the node further adds a bias to the total value, and applies an activation function to an addition result to obtain output of the node. This process is sequentially performed from the input layer to the output layer to obtain output of the neural network. Learning by the neural network is a process of determining an appropriate weight (bias included). There are various known methods of learning such as an error inverse propagation method, and these methods are widely applicable to the present embodiment.

More specifically, the neural network according to the present embodiment is a convolutional neural network (CNN) suitable for image recognition processing. The CNN includes a convolution layer that performs a convolution operation and a pooling layer. The convolution layer is a layer that performs filter processing. The pooling layer is a layer that performs a pooling operation for reducing sizes in a vertical direction and a lateral direction. An output layer of the CNN is a widely known softmax layer, for example. Specific configurations of the CNN may be implemented in various modified manners as to a number of convolution layers, a number of pooling layers, a mode of the output layer, or the like. The weight of the convolution layer of the CNN is a parameter of a filter. That is, learning by the CNN includes learning of a filter used for the convolution operation. The neural network including the CNN is a widely known method and any further detailed description is omitted. The machine learning according to the present embodiment is not limited to the method using the neural network. For example, as for the method of the machine learning according to the present embodiment, machine learning using various widely known methods, such as a support vector machine (SVM), is applicable. In addition, machine learning using methods that are improvements of these methods is also applicable.

In a step S11, the processing section 51 reads out the training data from the storage section 52. For example, one training image and corresponding flag data are read out for one inference. However, a plurality of training images and corresponding flag data may be used for one inference.

In a step S12, the processing section 51 infers a position and shape of an object, and outputs a result. That is, the processing section 51 inputs the training image to the neural network. The processing section 51 performs an inference process by the neural network to output flag data indicating the position and shape of the object.

In a step S13, the processing section 51 compares the inferred position and shape with the position and shape indicated by the annotation, and calculates an error based on a comparison result. That is, the processing section 51 calculates an error between the flag data output from the neural network and the flag data of the training data.

In a step S14, the processing section 51 adjusts a model parameter of the training model to reduce the error. That is, the processing section 51 adjusts a weight coefficient or the like between the nodes of the neural network based on the error obtained in the step S13.

In a step S15, the processing section 51 determines whether parameter adjustment is completed a predetermined number of times. When the parameter adjustment is not completed the predetermined number of times, the processing section 51 performs the steps S11 to S15 again. When the parameter adjustment is completed the predetermined number of times, the processing section 51 terminates the learning process as described in a step S16. Alternatively, the processing section 51 determines whether the error obtained in the step S13 becomes equal to or lower than a predetermined value. When the error is not equal to or lower than the predetermined value, the processing section 51 performs the steps S11 to S15 again. When the error becomes equal to or lower than the predetermined value, the processing section 51 terminates the learning process as described in the step S16. As a result of the process described above, the trained model is output as a learning result.

Figure 16:
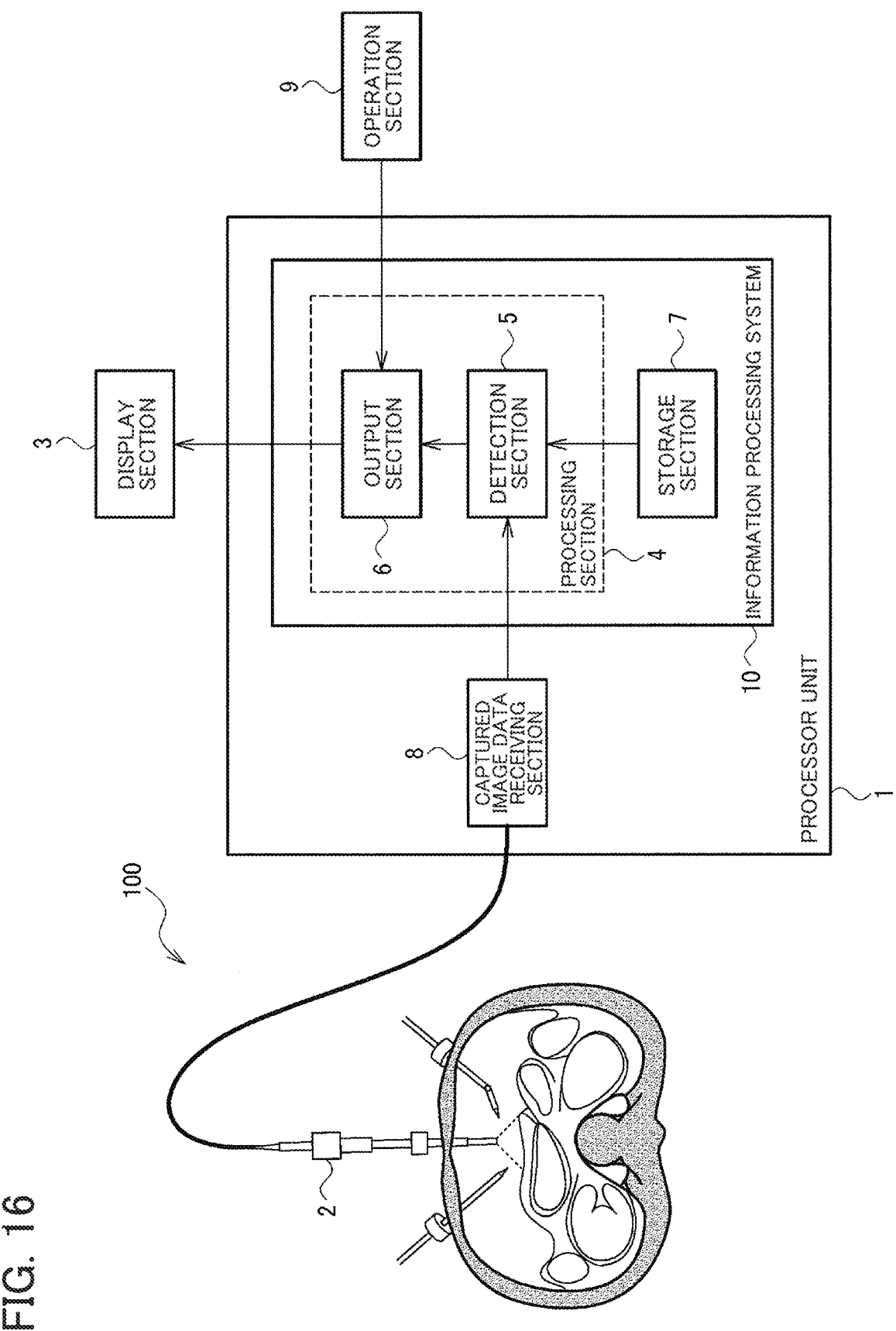
FIG. 16 is a configuration example of an endoscope system including an information processing system.

FIG. 16 is a configuration example of the information processing system 10, and an endoscope system 100 including the information processing system 10. The information processing system 10 is a inference device that performs the inference process using the trained model. The endoscope system 100 includes a processor unit 1, the endoscopic scope 2, and a display section 3. The endoscope system 100 may further include an operation section 9.

The endoscopic scope 2 includes an imaging device on its distal end portion that is inserted into an abdominal cavity. The imaging device captures an image in the abdominal cavity, and captured image data is transmitted from the endoscopic scope 2 to the processor unit 1.

The processor unit 1 is a device that performs various processes in the endoscope system 100. For example, the processor unit 1 performs control of the endoscope system 100 and image processing. The processor unit 1 includes a captured image data receiving section 8 that receives the captured image data from the endoscopic scope 2, and the information processing system 10 that detects an object from the captured image data based on the trained model.

The captured image data receiving section 8 is a connector to which a cable of the endoscopic scope 2 is connected, or an interface circuit that receives the captured image data, for example.

The information processing system 10 includes the storage section 7 that stores the trained model, and the processing section 4 that detects the object from the image based on the trained model stored in the storage section 7.

The storage section 7 is a storage device such as a semiconductor memory, a hard disk drive, or an optical disk drive. The storage section 7 stores the trained model in advance. Alternatively, a trained model may be input to the information processing system 10 via a network from an external device such as a server so as to be stored in the storage section 7.

The processing section 4 includes a detection section 5 that detects the object from the image by the inference based on the trained model, and an output section 6 that superimposes information about the object on the image based on a detection result, and causes the display section 3 to display a resultant. There may be various types of hardware that performs the inference based on the trained model. For example, the detection section 5 is a general purpose processor such as a CPU. In this case, the storage section 7 stores a program including an inference algorithm and a parameter used for the inference algorithm as the trained model. Alternatively, the detection section 5 may be a single purpose processor implementing the inference algorithm as hardware. In this case, the storage section 7 stores the parameter used for the inference algorithm as the trained model. The inference algorithm may use the neural network. In this case, the weight coefficient of the connection between the nodes in the neural network is the parameter.

The detection section 5 inputs the detection image captured by the endoscopic scope 2 to the trained model. The detection section 5 performs a detection process based on the trained model to detect the position and shape of the object in the detection image. That is, the detection result is output as detected flag data. The detected flag data is a flag map including pixels set with flags corresponding to the detected position and shape of the object. For example, similarly to the training data described referring to FIG. 11, four layers of the detected flag data corresponding to the respective objects are output.

The display section 3 is a monitor to display the image output from the output section 6, and is a display device such as a liquid crystal display, or an organic electroluminescence (EL) display.

The operation section 9 is a device used by the operator for operating the endoscope system 100. For example, the operation section 9 includes a button, a dial, a foot switch, or a touch panel. As will be described later, the output section 6 may change a display mode of the object based on input information from the operation section 9.

In the above description, the information processing system 10 is included in the processor unit 1, however, the information processing system 10 may partially or entirely disposed outside the processor unit 1. For example, the storage section 7 and the detection section 5 may be implemented by an external processing device such as a PC or a server. In this case, the captured image data receiving section 8 transmits the captured image data to the external processing device via a network or the like. The external processing device transmits information about the detected object to the output section 6 via the network or the like. The output section 6 superimposes the received information on the image and causes the display section 3 to display a resultant.

The method according to the present embodiment is applicable to the trained model that causes a computer to function to accept the detection image as input, perform the process of detecting the position of the given object from the detection image, and output the detection result. The trained model has been learned by the machine learning based on the training data in which the annotation data generated by the tracking method described above is associated with the frame image included in the video. The frame image associated with the annotation data may include all frames included in the video. However, the method according to the present embodiment is not limited to this, and the frame image associated with the annotation data may include some frames in the video. In this case, the machine learning is performed using the frame images associated with annotation data.

According to the tracking method in the present embodiment, the tracking is accurately performed with respect to the tagged region attached to the object in the video, so that highly accurate annotation data can be generated. As a result, performing the machine learning using the annotation data as the training data enables generation of the trained model that can implement a highly accurate detection process.

Furthermore, the method according to the present embodiment is applicable to the endoscope system 100 including the storage section 7 that stores the trained model described above, the endoscopic scope 2 that captures the detection image, and the processing section 4 that performs the process of detecting the position of the given object from the detection image based on the trained model.

As a result, a desired object can be accurately detected from the detection image. Specifically, the machine learning is performed using the training data including the annotation data attached to the object whose position and shape are not clearly displayed in the image, so that detection of the object based on the tacit knowledge of the skilled surgeon or the like can also be implemented. At this time, since the training data can be generated by tracking, a load of the surgeon or the like for the annotation can be reduced.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A tracking device comprising a processor including hardware,
   the processor being configured to:
   set a start frame to start tracking of a tracking target in a video including multiple frames;
   extract multiple representative points of a contour of the tracking target in the start frame;
   track the extracted multiple representative points in frames subsequent to the start frame;
   perform outlier determination on the tracked multiple representative points based on an interrelationship of the multiple representative points;
   perform a process of removing an outlier representative point that is a representative point determined to be an outlier;
   update the representative points by extracting new representative points based on multiple representative points after the process of removing the outlier representative point, in a case where any frame subsequent to the start frame meets a given condition; and
   determines a deviation degree of a first representative point of the multiple representative points based on any one of relative distance information between the first representative point and one or more of the representative points adjacent in a direction along the contour, and a curvature of a curve formed by the first representative point and some of the representative points adjacent in the direction along the contour, so as to determine whether the first representative point is the outlier representative point.

2. The tracking device as defined in claim 1, wherein the processor extracts multiple representative points of a contour of a tag region tagged as the tracking target to the start frame.

3. The tracking device as defined in claim 1, wherein
the processor extracts the multiple representative points from the contour of the tracking target such that adjacent representative points are spaced apart at a given interval.

4. The tracking device as defined in claim 1, wherein
the processor extracts the multiple representative points such that, on the contour of the tracking target, a density of representative points at a portion with a large curvature of the contour is higher than a density of representative points at a portion with a small curvature of the contour.

5. The tracking device as defined in claim 1, wherein
the processor extracts the new representative points based on the multiple representative points after the process of removing the outlier representative point, when a number of representative points becomes equal to or smaller than a given number threshold value due to the process of removing the outlier representative point and generates a closed curve based on the multiple representative points after the process of removing the outlier representative point, and extracts the new representative points from the generated closed curve.

6. The tracking device as defined in claim 1, wherein
the processor extracts the new representative points based on the multiple representative points after the process of removing the outlier representative point, when reliability of a tracking result becomes equal to or lower than a given reliability threshold value.

7. The tracking device as defined in claim 1, wherein
the processor extracts the new representative points based on the multiple representative points after the process of removing the outlier representative point at a given time interval.

8. The tracking device as defined in claim 1, wherein
the processor generates annotation data in which an inside of a closed curve generated based on the tracked multiple representative points is defined as an annotation region for each frame subsequent to the start frame.

9. An endoscope system comprising:
a memory that stores a trained model;
an endoscopic scope that captures a detection image; and
a processor that accepts the detection image as input, and performs a process of detecting a position of a given object from the detection image by using the trained model,
the trained model having been trained by machine learning based on training data in which annotation data is associated with a frame image in a video,
the annotation data being generated by:
acquiring the video including multiple frames;
setting a start frame to start tracking of a tracking target;
extracting multiple representative points of a contour of the tracking target in the start frame;
tracking the extracted multiple representative points in frames subsequent to the start frame;
performing outlier determination on the tracked multiple representative points based on an interrelationship of the multiple representative points;
performing a process of removing an outlier representative point that is a representative point determined to be an outlier;
updating the representative points by extracting new representative points based on multiple representative points after the process of removing the outlier representative point, in a case where any frame subsequent to the start frame meets a given condition;
determining a deviation degree of a first representative point of the multiple representative points based on any one of relative distance information between the first representative point and one or more of the representative points adjacent in a direction along the contour, and a curvature of a curve formed by the first representative point and some of the representative points adjacent in the direction along the contour, so as to determine whether the first representative point is the outlier representative point; and
generating the annotation data in which an inside of a closed curve generated based on the tracked multiple representative points is defined as an annotation region for each frame subsequent to the start frame.

10. A tracking method comprising:
acquiring a video including multiple frames;
setting a start frame to start tracking of a tracking target;
extracting multiple representative points of a contour of the tracking target in the start frame;
tracking the extracted multiple representative points in frames subsequent to the start frame;
performing outlier determination on the tracked multiple representative points based on an interrelationship of the multiple representative points;
performing a process of removing an outlier representative point that is a representative point determined to be an outlier;
updating the representative points by extracting new representative points based on multiple representative points after the process of removing the outlier representative point, in a case where any frame subsequent to the start frame meets a given condition; and
determining a deviation degree of a first representative point of the multiple representative points based on any one of relative distance information between the first representative point and one or more of the representative points adjacent in a direction along the contour, and a curvature of a curve formed by the first representative point and some of the representative points adjacent in the direction along the contour, so as to determine whether the first representative point is the outlier representative point.

* * * * *